United States Patent [19]

Ayon-Covarrubias

[11] Patent Number: 6,080,744

[45] Date of Patent: Jun. 27, 2000

[54] TOPICAL ANTIFUNGAL TREATMENT

[76] Inventor: Blas Ayon-Covarrubias, P.O. Box 39, Nyarit, Mexico, 63740

[21] Appl. No.: 09/247,954

[22] Filed: Feb. 10, 1999

[51] Int. Cl.⁷ .................. A61K 31/50; A61K 31/495; A61K 31/20; A61K 31/35; A61K 31/415

[52] U.S. Cl. .................. 514/252; 514/460; 514/396; 514/481; 514/558

[58] Field of Search .................. 424/401, 195.1, 424/430, 433, 464; 514/252, 460, 396, 481, 558

[56] References Cited

U.S. PATENT DOCUMENTS

| | | | |
|---|---|---|---|
| 2,832,126 | 4/1958 | Vandeputte | 167/65 |
| 3,334,126 | 8/1967 | Mayazaki et al. | 260/455 |
| 3,517,100 | 6/1970 | Renella | 424/123 |
| 3,705,172 | 12/1972 | Buchel et al. | 260/309 |
| 3,717,655 | 2/1973 | Godefroi et al. | 260/309 |
| 4,144,346 | 3/1979 | Heeres et al. | 424/273 R |
| 4,223,036 | 9/1980 | Heeres et al. | 424/269 |
| 4,810,499 | 3/1989 | DiMeglio | 424/195.1 |
| 5,648,399 | 7/1997 | Friedman et al. | 514/772.6 |
| 5,837,254 | 11/1998 | Chen | 424/195.1 |

OTHER PUBLICATIONS

Drug facts and comparisons, 51st edition, Anti-fungal agent, p. 2920–2942, 1997

Kiss et al., New combination for the therapy of . . . , Journal of Small Animal Practice, vol. 38(2), p. 57–60, 1997.

*Primary Examiner*—Marianne M. Cintins
*Assistant Examiner*—Vickie Kim
*Attorney, Agent, or Firm*—Trapani & Molldrem

[57] ABSTRACT

A topical mycological treatment composition for medical, veterinarian, or dental use contains as active ingredients clotrimazole, ketoconazole, micanazole, nystatin, tolnaftate, propionic acid, sodium propionate, undecelynic acid, and zinc undecelynate. These ingredients are contained in a natural cream base, and the base may also contain an anti-inflammatory agent and an antibacterial agent.

12 Claims, No Drawings

TOPICAL ANTIFUNGAL TREATMENT

BACKGROUND OF THE INVENTION

This invention relates to a composition for the treatment of mycotic infections, and to methods of treating such infections. The invention is more specifically concerned with a novel treatment composition that comprises a blend of active antimycotic ingredients in a natural, soothing base, in which the composition is capable of defeating a wide range of fungi and can clear topical fungal infections rather speedily.

A number of anti-fungal creams are now in use, and employed for a variety of dermatological and other mycotic infections, i.e., tinea pedis, tinea corporis, tinea capitis, etc. However. many types of such fungal infections have proven to be persistent and defeat any attempts to control or cure them. In addition, many of the fungi involved can spread from one person to another, and this is especially the case in geographical regions where cleansing and sanitation are difficult to carry out. Furthermore, many fungal infections that commence as topical infections, if left unchecked, can invade the body and cause grave illness or death.

Many of the health problems associated with various fungal infections, as well as bacterial and viral infections, are discussed in Friedman U.S. Pat. No. 5,648,399. It is clearly recognized that fungal infections are a major health risk, and affect not only the skin, but also the oral cavity and other places on the body. Friedman is of interest for its discussion of various fungi that have been identified with human infection, such as *Candida albicans, C. tropicalis, C. stellatoidea, C. pseudotropicalis, C. parapsilosis, C. stellatoidea, C. guillieromondii, C. krusei, C. vixwanathii, T orulopsis glabrata, Geotrichium candidum, Cryptococcus neoformans, Blastomyces dermatides, Paracoccidioides brasiliensis, Sporothrix schenkii, Rhinosporidium seeberi, Histoplasma capsulatum, Histoplasma duboisii, Coccidiodes immities, Trichophyton mentagrophytes, T. rubrum, T. tonsurans,* and *T. violaceum. Aspergillus fumigatus* is another fungus that can invade the human skin and other tissues, including the eyes. Friedman is also valuable for its extensive bibliographical list of references on this and related topics.

Topical treatment of human fungal infections normally employ a single antifungal agent in a base or carrier. The base can be a cream or salve, but in some cases, the agent is incorporated into a time release vehicle. However, the results of treatment have been spotty and inconsistent, with some patients experiencing recurrence of the flora, and some persons receiving no relief from the infection. Consequently, a more effective approach to this problem has long been sought.

OBJECTS AND SUMMARY OF THE INVENTION

Accordingly, it is an object of the present invention to provide a topical antimycotic treatment that is more effective than what has been available in the prior art, and which is effective for a wide variety of mycological illnesses.

It is another object to provide a topical antimycotic treatment that brings about speedy relief to persons suffering from fungal infections.

In accordance with one aspect of the present invention, a novel topical treatment composition is formed of a natural base, e.g., an all-natural cream base, and includes the following active antimycotic ingredients, per 100 grams of the cream base: ketaconazole—0.1 to 3 grams; nystatin—$1*10^5$ to $2*10^7$ units; miconazole nitrate—0.1 to 2.0 grams; tolnaftate—0.05 to 1.0 grams; chlotrimazole—0.05 to 1.0 grams; undecenoic acid—0.1 to 5 grams; undecylenic acid zinc salt—0.5 to 8 grams; propionic acid—0.1 to 3 grams; and sodium propionate—1 to 8 grams. The composition is applied to the affected area and then is periodically re-applied until the fungal infection has cleared. Noticeable results occur within about one week, even for rather advanced cases, and the infection is often cleared within about four weeks. Gentamicin may be present in an amount of 0.01 to 0.5 grams per 100 grams of the cream base as an antibacterial agent, and dipropionate betamethasone may be present in an amount of 0.01 to 0.5 grams per 100 grams of the base as an anti-inflammatory agent.

Here, one milligram of nystatin is considered to equal 4,760 pharmaceutical units.

The above and many other objects, features, and advantages of this invention will be more fully appreciated from the ensuing description of a preferred embodiment.

DETAILED DESCRIPTION OF A PREFERRED EMBODIMENT

The following has proven to be a particularly effective cream-based topical treatment for fungal infections of human patients. The ingredients are given for 100 grams of the cream base: ketaconazole—0.1 to 3 grams; nystatin—$1*10^5$ to $2*10^7$ units; miconazole nitrate—0.1 to 2 grams; tolnaftate—0.05 to 1 grams; chlotrimazole—0.05 to 1 grams; undecenoic acid—0.1 to 5 grams; undecylenic acid zinc salt—1 to 8 grams; propionic acid—0.5 to 2 grams; and sodium propionate—2 to 8 grams. These ingredients can preferably be in the ranges: ketaconazole—0.2 to 2 grams; nystatin—$2*10^5$ to $1*10^7$ units; miconazole nitrate—0.2 to 1.5 grams; tolnaftate—0.1 to 0.5 grams; chlotrimazole—0.1 to 0.5 grams; undecenoic acid—0.5 to 5 grams; undecylenic acid zinc salt—0.5 to 8 grams; propionic acid—0.1 to 3 grams; and sodium propionate—1 to 8 grams. This treatment composition can be made according to the following examples:

EXAMPLE I

In 100 grams of the cream base, ketoconazole, 1.5 grams; nystatin, 9,000,000 units (i.e., 1.972 g); miconazole nitrate, 1.0 grams; tolnaftate, 0.5 grams; chlotrimazole, 0.5 grams; undecenoic acid, 3.0 grams; undecylenic acid zinc salt, 8.0 grams; propionic acid, 2.0 grams; and sodium propionate, 8.0 grams. In this case, the cream base can comprise beeswax, 12%; lecithin, 13%; canola oil, 26%; vitamin E, 5%; lavender oil, 5%; glycerol, 15%; and aloe vera gel, 25% (these figures may differ from 100%, due to rounding errors). Instead of lavender oil, oil of wintergreen or another essential oil can be used.

EXAMPLE II

Here, the cream base is the same as in Example I, and the active ingredients are listed per 200 grams of the cream base: Ketoconazole, 0.8 grams; nystatin, 6,000,000 units; miconazole nitrate, 0.4 grams; tolnaftate, 0.3 grams; chlotrimazole, 0.4 grams; undecenoic acid, 1.5 grams; undecylenic acid zinc salt, 4.0 grams; propionic acid, 1.2 grams; and sodium propionate, 4 grams. In addition gentamicin and dipropionate betamethasone were present in amounts of 0.04 grams and 0.08 grams, respectively. The first serves as an antibacterial agent to combat subsidiary infections, and the second is an anti-inflammatory agent to speed healing and to provide some relief from pain and itch.

EXAMPLE III

Employing the same cream base as in Example I, the active ingredients are present as listed here per 100 grams of cream base: ketoconazole, 1.5 grams; nystatin, 9,000,000 units; miconazole nitrate, 1.0 grams; tolnaftate, 0.5 grams; chlotrimazole, 0.5 grams; undecenoic acid, 3.0 grams; undecylenic acid zinc salt, 8.0 grams; propionic acid, 2.0 grams; and sodium propionate, 8.0 grams. Gentamicin and dipropionate betamethasone are also present in units of 0.05 grams each per 100 grams of cream, as antibacterial agent and anti-inflammatory agent, respectively.

The cream base is intended as a natural base, without artificial ingredients, and with no animal ingredients (such as lanolin) that may cause irritation. In some cases, the vegetable oil can be extra virgin olive oil, rather than canola oil. Animal oil and mineral oil have been used previously to make a base. However, the use of natural cream base would further protect and help in healing and penetration of medication.

The treatment has been tested and found effective in the laboratory against a number of fungi, including *Candida albicans, Blastomyces dermatidis, Aspergillus fumigatus, Cryptococcus neoformans, Trichophytan mentagraphytes*, and *Microsporum canis*. In each case, cultures of these fungi were grown in vitro, in medium in Petri dishes under controlled conditions. For each fungus mentioned above, there was a control dish containing medium alone and a test dish containing the same medium but with the creme composition of Example II present in an amount of 5 g/100 ml. Living fungus was applied to each dish. After a test period of seven days, it was observed for each species tested that there was active flora in the control dish, but the fungus was completely halted in the test dish. The treatment composition in an amount as low as 1 gm/100 ml was also very effective in inhibiting the growth of the above fungi.

The composition of Example I has been used in the treatment of advanced dermatological disorders of the hands, feet, and face. The patients involved had experienced great discomfort, and the infections had not responded to any previous medical treatments. The composition was applied to the affected areas of these patients one or two times a day. After a period of four weeks, the infection was cleared, with no noticable discoloration, no foliation, and no itching. A similar observation was made where an individual patient had a severe athletes foot (tinea pedis) infection, shich showed no response to Nizoral treatment prescribed by a physician. Upon treatment with this cream composition, the infection was cleared in between four and five weeks. Similar cases of rapid clearance have been observed in other patients as well.

While the invention has been described with reference to specific preferred embodiments, the invention is certainly not limited to those precise embodiments. Rather, many modifications and variations will become apparent to persons of skill in the art without departure from the scope and spirit of this invention, as defined in the appended claims.

I claim:

1. A novel topical treatment composition for a mycotic infection comprising a blend of active antifungal ingredients carried in a base, said antifungal ingredients being in the following amounts per 100 grams of said base:

ketaconazole—0.1 to 3 grams;
   nystatin—$1*10$ to $2*10^7$ units;
   miconazole nitrate—0.1 to 2.0 grams;
   tolnaftate—0.05 to 1 grams;
   clotrimazole—0.05 to 1 grams;
   unidecenoic acid—0.1 to 5 grams;
   undecylenic acid zinc salt—0.5 to 8 grams;
   propionic acid—0.1 to 3 grams; and
   sodium propionate—1 to 8 grams.

2. The topical treatment composition of claim 1, also comprising an antibacterial agent in an effective amount.

3. The topical treatment composition of claim 2 wherein said antibacterial agent includes gentamicin in an amount of 0.01 to 0.5 grams per 100 grams of said base.

4. The topical treatment composition of claim 1, also comprising an antiinflammatory agent in an effective amount.

5. The topical treatment composition of claim 4 wherein said anti-inflammatory agent includes dipropionate betamethasone in an amount of 0.01 to 0.5 grams per 100 grams of said base.

6. The topical treatment composition of claim 1 werein said base is a natural cream base.

7. The topical treatment composition of claim 6 wherein said cream base comprises a blend of beeswax; lecithin; a natural vegetable oil; vitamin E; an essential oil; glycerol; and aloe vera gel.

8. A novel method of treating a topical fungal infection in a patient, comprising applying to said patient a treatment composition formed of a neutral base and including the following active antimycotic ingredients, per 100 grams of said base: ketaconazole—0.1 to 3 grams; nystatin—$1*10^5$ to $2*10^7$ units; miconazole nitrate—0.1 to 2.0 grams; tolnaftate—0.05 to 1.0 grams; clotrimazole—0.05 to 1.0 grams; undecenoic acid—0.1 to 5 grams; undecylenic acid zinc salt—0.5 to 8 grams; propionic acid—0.1 to 3 grams; and sodium propionate—1 to 8 grams; and periodically re-applying said treatment composition until the fungal infection has cleared.

9. The method of claim 8, wherein said treatment composition also includes an effective amount of an antibacterial agent.

10. The method of claim 8, wherein said treatment composition also includes an effective amount of an anti-inflammatory agent.

11. The method of claim 8, wherein said base includes a natural cream.

12. The method of claim 11, wherein said neutral cream includes a blend of beeswax; lecithin; a natural vegetable oil; vitamin E; an essential oil; glycerol; and aloe vera gel.

* * * * *